(12) United States Patent
Rowe

(10) Patent No.: US 9,292,916 B2
(45) Date of Patent: Mar. 22, 2016

(54) METHODS AND SYSTEMS FOR ESTIMATING GENETIC CHARACTERISTICS FROM BIOMETRIC MEASUREMENTS

(75) Inventor: Robert K. Rowe, Corrales, NM (US)

(73) Assignee: HID Global Corporation, Austin, TX (US)

( * ) Notice: Subject to any disclaimer, the term of this patent is extended or adjusted under 35 U.S.C. 154(b) by 0 days.

(21) Appl. No.: 13/569,895

(22) Filed: Aug. 8, 2012

(65) Prior Publication Data

US 2013/0202182 A1 Aug. 8, 2013

Related U.S. Application Data

(60) Provisional application No. 61/521,510, filed on Aug. 9, 2011, provisional application No. 61/522,389, filed on Aug. 11, 2011, provisional application No. 61/537,445, filed on Sep. 21, 2011.

(51) Int. Cl.
*G06K 9/00* (2006.01)
*G06T 7/00* (2006.01)
*A61B 10/02* (2006.01)

(52) U.S. Cl.
CPC ............... *G06T 7/0012* (2013.01); *A61B 10/02* (2013.01); *G06K 9/00046* (2013.01); *G06K 9/00892* (2013.01); *G06K 9/00899* (2013.01)

(58) Field of Classification Search
None
See application file for complete search history.

(56) References Cited

U.S. PATENT DOCUMENTS

| 3,508,830 | A | * | 4/1970 | Hecht et al. | 356/338 |
| 5,249,370 | A | * | 10/1993 | Stanger | A47K 10/48 34/202 |
| 5,732,148 | A | | 3/1998 | Keagy et al. | |
| 6,061,463 | A | | 5/2000 | Metz et al. | |
| 6,091,837 | A | * | 7/2000 | Dinh | 382/124 |
| 7,627,151 | B2 | * | 12/2009 | Rowe | 382/124 |
| 7,640,051 | B2 | | 12/2009 | Krishnan et al. | |
| 7,787,110 | B2 | * | 8/2010 | Raguin | G06K 9/00046 356/71 |
| 8,269,855 | B2 | * | 9/2012 | Amir et al. | 348/229.1 |
| 8,649,001 | B2 | * | 2/2014 | Wu et al. | 356/71 |
| 8,731,250 | B2 | * | 5/2014 | Martin et al. | 382/124 |
| 2003/0060692 | A1 | * | 3/2003 | Ruchti et al. | 600/310 |
| 2006/0110015 | A1 | * | 5/2006 | Rowe | 382/124 |
| 2006/0276966 | A1 | | 12/2006 | Cotton et al. | |
| 2007/0207549 | A1 | * | 9/2007 | Sangha et al. | 436/63 |
| 2010/0098831 | A1 | * | 4/2010 | Anderson | 427/1 |
| 2010/0284574 | A1 | * | 11/2010 | Fenrich et al. | 382/116 |
| 2013/0142413 | A1 | * | 6/2013 | So | G06K 9/00127 382/133 |

OTHER PUBLICATIONS

Applicant: LUMIDIGM, INC. Notification of Transmittal of the International Search Report and the Written Opinion of the International Searching Authority, or the Declaration. International Application No. PCT/US2012/050190. International Filing Date: Aug. 9, 2012.

\* cited by examiner

*Primary Examiner* — Nancy Bitar
(74) *Attorney, Agent, or Firm* — Marsh Fischmann & Breyfogle LLP; Jonathon A. Szumny

(57) ABSTRACT

Methods and devices are disclosed for collecting fingerprint and genetic information from an individual during a single collection session. A skin site is illuminated by direct imaging of the skin site using light reflected from the illuminated skin site. A cell of the individual, such as a skin cell, is retrieved from the collection surface.

20 Claims, 11 Drawing Sheets

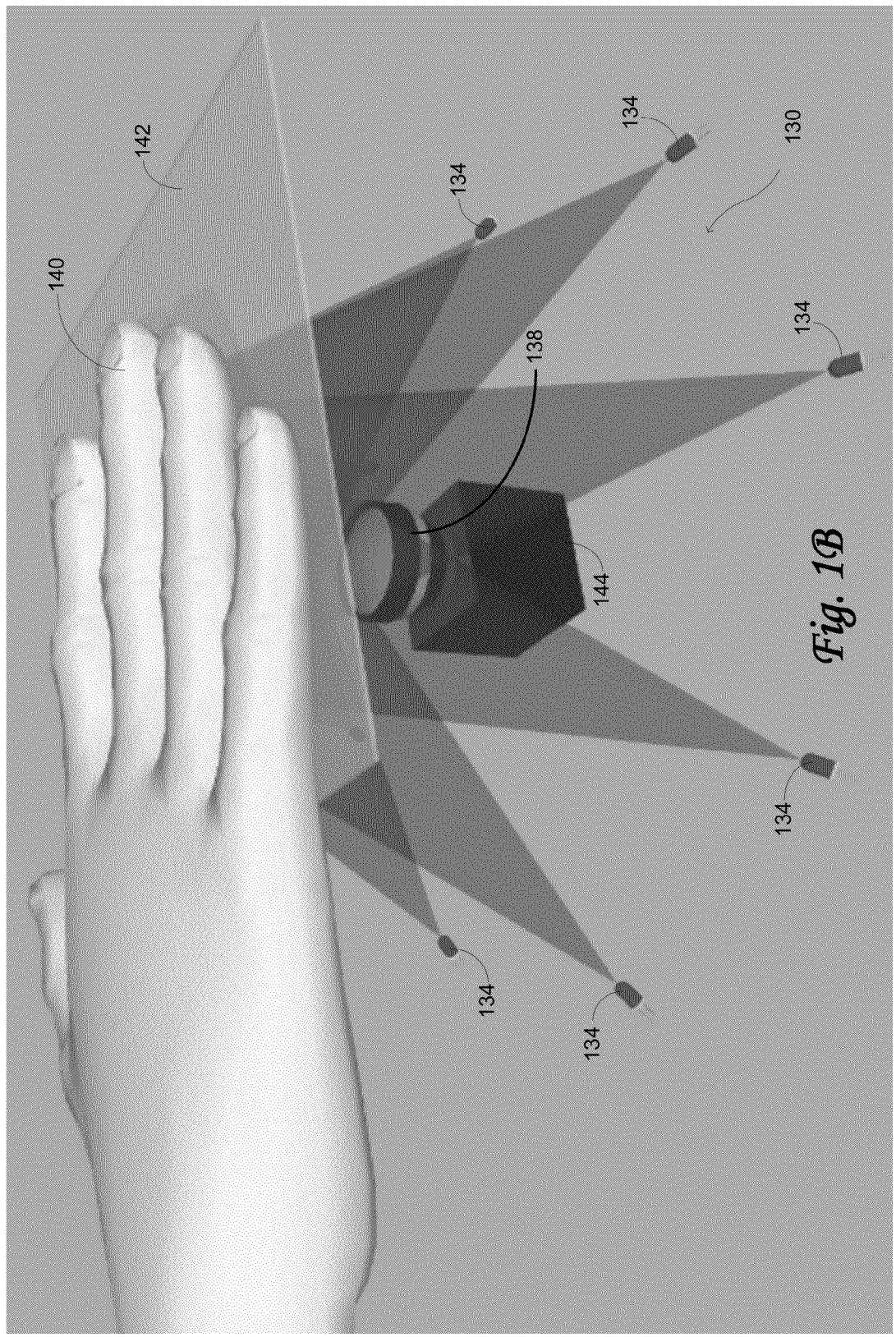

METHODS AND SYSTEMS FOR ESTIMATING GENETIC CHARACTERISTICS FROM BIOMETRIC MEASUREMENTS

CROSS-REFERENCE TO RELATED APPLICATIONS

This application is a nonprovisional of each of the following applications, each of which is hereby incorporated by reference for all purposes: U.S. Prov. Pat. Appl. No. 61/521,510, entitled "METHODS AND SYSTEMS FOR ESTIMATING GENETIC CHARACTERISTICS FROM BIOMETRIC MEASUREMENTS," filed Aug. 9, 2011 by Robert K. Rowe; U.S. Prov. Pat. Appl. No. 61/522,389, entitled "METHODS AND SYSTEMS FOR ESTIMATING GENETIC CHARACTERISTICS FROM BIOMETRIC MEASUREMENTS," filed Aug. 11, 2011 by Robert K. Rowe; and U.S. Prov. Pat. Appl. No. 61/537,445, entitled "METHODS AND SYSTEMS FOR ESTIMATING GENETIC CHARACTERISTICS FROM BIOMETRIC MEASUREMENTS," filed Sep. 21, 2011 by Robert K. Rowe.

BACKGROUND OF THE INVENTION

This application relates generally to biometrics. More specifically, this application relates to methods and systems for estimating genetic characteristics of individuals from biometric measurements.

"Dermatoglyphics" refers generally to the scientific study of ridge and valley patterns on skin, usually primate skin. In human beings, the skin on the fingers, palms, toes, and soles is ridged, and the characteristic pattern of such "fingerprints" is well known to be used in the identification applications because the specific pattern on an individual is unique. Other mammals show similar patterns on the corresponding surfaces of their paws and some primates are known to have ridged skin along the tail.

Traditionally, the ridge and valley patterns have been collected for identification applications by applying ink so that a copy of the pattern may be stored on appropriate physical media. More recently, digitized versions of the patterns have been stored electronically. In either case, storage of a database of patterns enables a comparison with a pattern supplied by an individual to verify his purported identity or enables a scan of the database of patterns to attempt identification of a pattern belonging to an otherwise unknown individual. The development of digitized versions have beneficially allowed sophisticated pattern-comparison algorithms to be used in searching large numbers of stored patterns to facilitate law-enforcement, immigration, and other processes.

In addition to being unique, it is also known that the characteristic patterns, which are referred to generically herein as "fingerprints," irrespective of the location of the skin site where they appear, may be related to certain genetic disorders. Because the patterns develop during a critical period of embryogenesis when the architecture of an individual's major organ systems is developing, correlations may exist between chromosomal abnormalities that affect the organ systems and the presence of certain dermatoglyphic features. For example, dermatoglyphic correlations with the genetic disorder of Down syndrome, caused by the full or partial presence of an extra 21st chromosome, were established well before the chromosomal basis for diagnosis. Those with Down syndrome have mainly ulnar loops and significantly different triradial angles in their fingerprints than do those who are unaffected by the syndrome. The predominance of whorls has been associated with Turner syndrome. Excess arches on the fingertips have been associated with Patau syndrome. Still other, more complex systemic patterns have been correlated with the presence of other genetic disorders.

With the development of practical genetic testing, relatively little research on establishing correlations between dermatoglyphic patterns and genetic disorders has continued, and the correlations that are known rely on very coarse, simple features like the number of triradii, ridge count, number of whorl patterns, asymmetries across hands, etc. These forms of classification are largely based on the features originally established by Sir Francis Galton in the 19th century.

A more sophisticated classification of dermatoglyphic patterns, coupled with an analysis of their correlations with genetic disorders, would enable preliminary assessments of genetic disorders to be made very easily and noninvasively through the collection and analysis of fingerprints.

SUMMARY

In a first set of embodiments, methods are provided for collecting fingerprint and genetic information from an individual during a single collection session. A skin site is illuminated by direct imaging of the skin site using light reflected from the illuminated skin site. A cell of the individual, such as a skin cell, is retrieved from the collection surface.

In some of these embodiments, the collection surface is comprised by a single-use collection membrane at least partially transparent to the light, with the skin site being illuminated by directing light through the collection membrane to the skin site. The collection membrane may then be replaced in preparation for collecting fingerprint and genetic information from a second individual during a second collection session. In some instances, the collection surface includes a chemical or includes an adhesive or abrasive property. Heat, pressure, airflow, motion, or other effects may be applied to the skin site to promote collection.

The skin site may be illuminated under a plurality of distinct optical conditions, and obtaining the image of the skin site may comprise generating a topographic representation of the skin site.

In some embodiments, the collection membrane may be placed on the skin site, such as where it comprises an adhesive strip placed on a body part or where it comprises a glove or finger cot when the skin site comprises part of a hand. The collection membrane may comprise a marking, with obtaining an image of the skin site comprising also obtaining an image of the marking. In one embodiment, the collection membrane comprises a conformal coating having a topography that substantially matches a topography of the skin site, with obtaining an image of the skin site comprising obtaining an image of the conformal coating. In a specific embodiment, the conformal coating is substantially opaque to the light.

These methods may also be embodied in a sensor that comprises an illumination system, a detection system, a single-use collection membrane, and a computational unit. The illumination system is disposed to direct light to a skin site of an individual. The detection system is disposed to receive light reflected from the skin site. The collection membrane, which may be at least partially transparent to the light, is adapted to contact the skin site during illumination of the skin site and to collect a cell from the individual. The computational unit is interfaced with the illumination system and with the detection system, and has instructions to operate those systems in implementing the methods described above.

In another set of embodiments, methods are provided of establishing a relationship between fingerprint features and medical assessments. A fingerprint is obtained from each of a plurality of individuals drawn from a representative population, and a respective medical assessment is developed for each of the plurality of individuals. An associative machine-learning technique may be applied to the developed medical assessments and features to establish the relationship.

In some embodiments, development of the respective medical assessments may comprise obtaining a respective genetic sample from each of the plurality of individuals so that genetic markers may be extracted from the genetic samples. Application of the associative machine-learning technique then comprises applying it to the extracted features and the extracted genetic markers to establish the relationship.

The fingerprints may be obtained using the methods described above, including by using direct imaging of a skin site, by illuminating the skin site under a plurality of optical conditions, and/or by generating a topographic representation of the skin site. The genetic samples may be obtained by using a single-use collection membrane that is in at least partial contact with the skin site and that may be adhesive, abrasive, include a chemical, or include another structure that enhances collection. One example of an associative machine-learning technique that may be used comprises a neural-net technique.

In a further set of embodiments, methods are provided of medically screening an individual. An image is obtained of an external part of the individual, and features are extracted from the image. The extracted features are evaluated in accordance with an established relationship to estimate a medical characteristic of the individual, with the relationship having been established from a representative population through the application of an associative machine-learning technique to medical assessments and features over the representative population.

The image of the external part of the individual may comprise a fingerprint image of the individual, such as a newborn footprint image in a particular embodiment. In some instances, the image of the external part of the individual may further comprise an image of gross anatomic detail of a region of the individual that includes the fingerprint. Such fingerprint images may be obtained by illuminating a skin site of the individual that includes a fingerprint of the individual, and obtaining the fingerprint image by direct imaging of the skin site using light reflected from the skin site. As in other embodiments, the skin site may be illuminated under a plurality of distinct optical conditions and/or a topographic representation of the skin site may be generated. In an alternative embodiment, the image of the external part of the individual comprises an iris image of the image.

These methods may also be embodied in a sensor that comprises an imaging system and a computational unit. The computational unit is coupled with the imaging system and includes a representation of a relationship from a representative population through the application of on associative machine-learning technique to medical assessments and features over the representative population. The computational unit has instructions to implement the methods as described above.

A further set of embodiments provides a method for establishing a correspondence between a fingerprint of an individual and a sample to be associated with the individual. An image of a skin site of the individual and an image of an identifying mark associated with the sample are simultaneously acquired. The uniqueness of the mark may be confirmed. In some instances, an image of a container holding the sample is also acquired simultaneously with acquisition of the other images, and confirmation that the sample and/or the container have expected characteristics may be performed. The images may be acquired using a multispectral sensor.

BRIEF DESCRIPTION OF THE DRAWINGS

A further understanding of the nature and advantages of the present invention may be realized by reference to the remaining portions of the specification and the drawings, wherein like reference labels are used throughout the several drawings to refer to similar components. In some instances, reference labels in include a numerical portion followed by a latin-letter suffix; reference to only the numerical portion of a reference label is intended to refer collectively to all reference labels that have that numerical portion but different latin-letter suffices.

FIG. 1B provides a three-dimensional view illustrating a general configuration of an optical topographic imaging device used in another embodiment of the invention;

DETAILED DESCRIPTION OF EXEMPLARY EMBODIMENTS

Figure 1A:
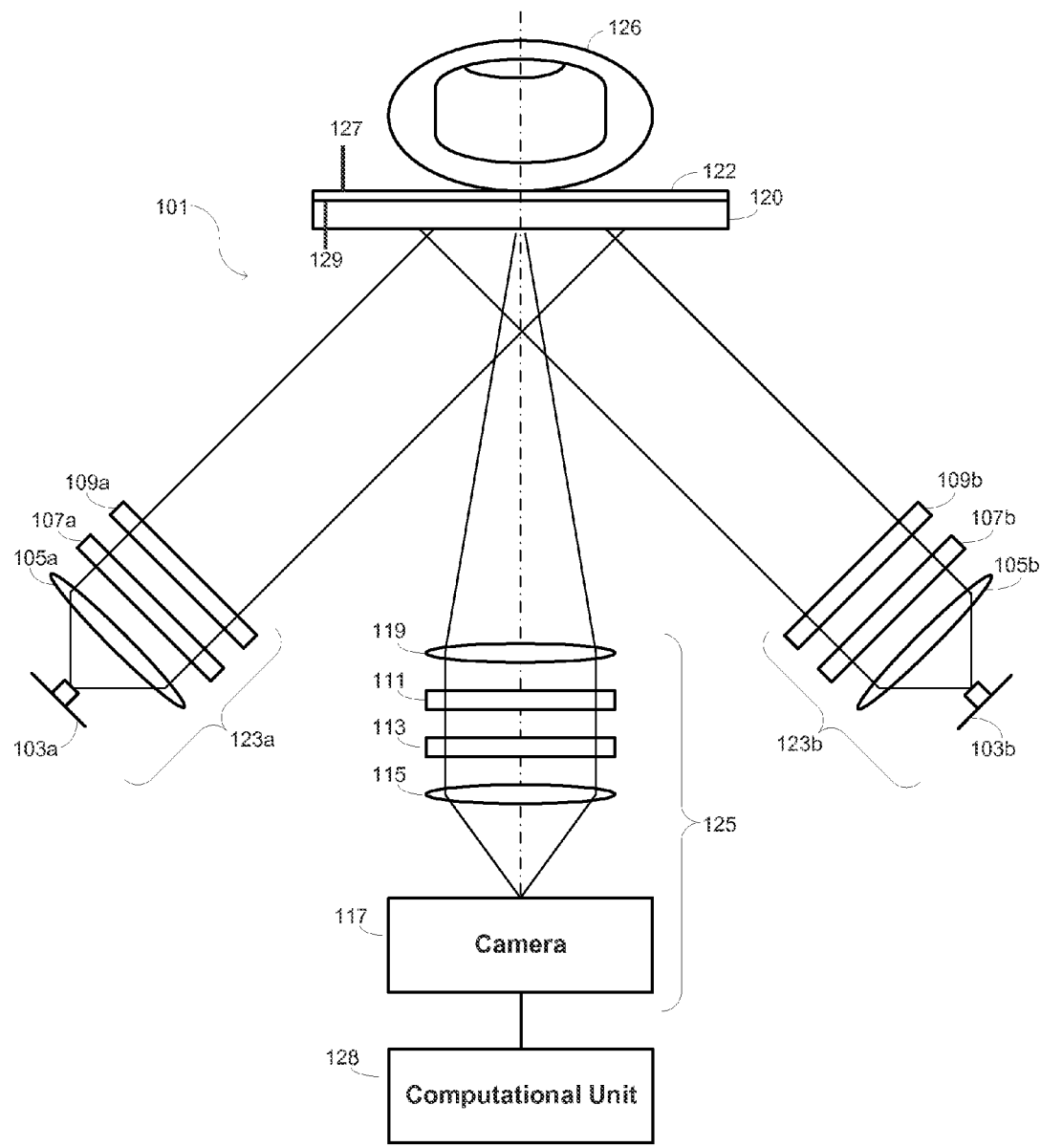
FIG. 1A provides a front view of a multispectral biometric sensor used in an embodiment of the invention.

Embodiments of the invention provide methods and systems that may be used to estimate genetic characteristics of individuals from biometric measurements, particularly from fingerprint measurements. As used herein, the term "fingerprints" is intended to refer to any topographical skin feature, irrespective of whether it occurs on a finger or on another part of the body. Applications of the invention may find utility not only when applied to topographical features present on the volar surfaces of fingers or hands, but also when applied to other skin locations. Specific examples of skin sites from which "fingerprints" may be extracted thus include all surfaces and all joints of the fingers and thumbs, all surfaces and joints of the toes, the fingernails or toenails and nail beds, the palms, the backs of the hands, the soles of the feet, the wrist and forearms, the face, the ears, areas around the eyes, and all other external surfaces of the body.

In some embodiments, information collected from the fingerprint may include information about spectral characteristics of the skin. Such spectral characteristics may be due to skin pigmentation, structural characteristics of the skin, a state of perfusion of the skin, or a combination of such sources. The spectral information may be collected in some embodiments and may be acquired and/or compiled on a variety of different measurement scales. For example, in the case of a simple color image of the skin, the overall skin tone may be summarized by one discrete or continuous value, which may then be included in subsequent analysis. Alternatively, some embodiments of the present invention are able to acquire separate images of skin topography and skin reflectance (in some cases reflectance at a plurality of wavelengths) as distinct images with similar resolution. In such cases, the reflectance image (also known as albedo) may be used in conjunction with or separately from the topographic image to perform the processing of the present invention.

Aspects of the invention includes a methodology by which correlations are established between genetic markers and dermatoglyphic features that is not constrained to the relatively simple historical features that have been used in the classification of fingerprints. Rather, generalized image features of the fingerprint images are used to quantify the presence and/or degree of such features in each fingerprint image. These image features may be developed through associative machine learning methods applied to a representative set of images (e.g., principal components), or may be pre-established features (e.g., wavelets), or some combination of both. The strength of such features may then be used to determine the strength of the correlation of those derived features with specific genetic markers. This is achieved through another aspect of the invention, which includes methods and systems that enable the simultaneous collection of genetic material and fingerprints. Systems that have attempted such simultaneous collection in the past have suffered from the need to have precise optical coupling among components of the system that are avoided by embodiments of the invention.

One example of a suitable system is illustrated schematically in front view by FIG. 1A. This embodiment takes the form of a multispectral sensor that may be used for simultaneous collection of biometric and genetic data from an individual. As used herein, "multispectral data" refers to the set of all images collected under a plurality of distinct optical conditions during a single illumination session. The different optical conditions may include differences in polarization conditions, differences in illumination angle, differences in imaging angle, and differences in illumination wavelength. Under some optical conditions, images may be affected by the presence and distribution of total-internal-reflectance ("TIR") phenomena at interfaces. Such images are referred to herein as "TIR images," and are distinguished from "direct images," which are images collected under optical conditions that are substantially unaffected by the presence or absence of TIR effects.

The multispectral sensor 101 includes an illumination subsystem 123 having one or more light sources 103 and a detection subsystem 125 with a camera 117. The drawing depicts an embodiment in which the illumination subsystem 123 comprises a plurality of illumination subsystems 123*a* and 123*b*, but there is no limitation on the number of illumination or detection subsystems 123 or 125 that may be included. For example, the number of illumination subsystems 123 may conveniently be selected to achieve certain levels of illumination, to meet packaging requirements, and to meet other structural constraints of the multispectral sensor 101. Illumination light passes from the source 103 through the illumination optics 105 that shape the illumination to a desired form, such as in the form of flood light, light lines, light points, and the like. The illumination optics 105 are shown for convenience as consisting of a lens but may more generally include any combination of one or more lenses, one or more mirrors, and/or other optical elements. The illumination optics 105 may also comprise a scanner mechanism (not shown) to scan the illumination light in a specified one-dimensional or two-dimensional pattern. The light source 103 may comprise a point source, a line source, an area source, or may comprise a series of such sources in different embodiments. In one embodiment, the illumination light is provided as polarized light, such as by disposing a linear polarizer 107 through which the light passes before being directed towards a skin site 126.

In some instances, the light source 103 may comprise one or more quasimonochromatic sources in which the light is provided over a narrow wavelength band. Such quasimonochromatic sources may include such devices as light-emitting diodes, laser diodes, or quantum-dot lasers. Alternatively, the light source 103 may comprise a broadband source such as an incandescent bulb or glow bar. In the case of a broadband source, the illumination light may pass through a bandpass filter 109 to narrow the spectral width of the illumination light. In one embodiment, the bandpass filter 109 comprises one or more discrete optical bandpass filters. In another embodiment, the bandpass filter 109 comprises a continuously variable filter that moves rotationally or linearly (or with a combination of rotational and linear movement) to change the wavelength of illumination light. In still another embodiment, the bandpass filter 109 comprises a tunable filter element such as a liquid-crystal tunable filter, an acousto-optical tunable filter, a tunable Fabry-Perot filter or other filter mechanism known to one knowledgeable in the art.

After the light from the light source 103 passes through the illumination optics 105, and optionally through the optical filter 109 and/or polarizer 107, it is directed towards the skin site 126. Although the skin site 126 is illustrated in the drawing as comprising a surface of a finger, the skin site may more generally comprise any skin site that includes a topographical feature as described above. Notably, in some embodiments, the skin site includes surfaces from multiple portions of a hand, such as surfaces from a plurality of fingers. The light is directed through a platen 120 and then through a single-use membrane 122 having first and second sides 127, 129 that face in respective opposite directions. Specifically, after the light has passed through the platen 120, the light is directed through the second side 129 of the membrane 122 and then through the first side 127 of the membrane 122 before reflecting from the skin site 126 which is positioned in a first position over and at least partially in contact with the first side 127 of the membrane 122. Preferably, the membrane 122 is substantially transparent at the wavelengths of the illumination light, but may be translucent at such wavelengths in alternative embodiments. The membrane 122 is preferably sterile and adapted to collect a sample on the first side 127 thereof that contains genetic material from the skin site. The genetic material may be in the form of DNA or RNA, and may originate in the nucleus or mitochondria of cells. Such a sample may thus include skin cells in addition to other types of cells that may be present at the skin site such as sebaceous-oil cells and other cells.

Different embodiments of the invention may include various mechanisms for promoting collection of the sample, and these mechanisms may be integrated with the structure of the membrane itself or may be provided in the form of structures supplementary to the membrane. For example, in some embodiments, the membrane 122 includes a chemical that may promote sample collection through any of a variety of mechanisms. In one specific embodiment, the chemical comprises an adhesive applied over a support surface so that skin cells adhere to the membrane when contacted by the skin site. Examples of support surfaces that may be used as part of the membrane 122 include a variety of synthetic resins such as cellulose, polypropylene, polyethylene, and PVC, among others. Adhesive techniques may alternatively be implemented structurally, such as in embodiments where the membrane comprises an adhesive-like biomimetic material such as recently developed films having polyimide hairs.

In other embodiments, the membrane includes a chemical chosen to promote secretions such as sebum or perspiration from the human body or to promote the sloughing of skin cells. While some secretions may not directly include genetic material in their composition, the increase in secretion itself acts to dislodge cells that do include genetic material, and which may be recovered from the collection membrane 122. In some embodiments a chemical exfoliant may be used to accelerate skin sloughing. There are numerous chemicals known to those of skill in the art that have these effects, and they may readily be applied in nontoxic concentrations to improve the effectiveness of genetic-material sample collection.

A variety of nonchemical mechanisms may also be used to promote similar effects of increasing the body's secretions at the skin site or of increasing the sloughing of skin cells from the skin site. Heat, for example, may be provided to increase perspiration through any of several mechanisms, including the use of resistive heating structures included near or in contact with the platen 120 or the use of radiant heating structures that focus heat towards the collection membrane 122. Pressure may also be used effectively to squeeze out sebaceous fluid and perspiration for deposit on the collection membrane 122. Such pressure may be applied by a mechanism coupled with the platen to press the collection membrane 122 against the skin site 126 when in contact with the skin site, or could be applied by the imposition of collection protocols. For instance, an individual presenting a skin site 126 could be instructed to press firmly on the sensor 101 in a manner similar to the collection of conventional ink-and-paper fingerprints, even though unnecessary for high-quality imaging of the skin site 126. Alternatively, a technician could aid in use of the sensor, taking the individual's finger or other body part and pressing it firmly on the sensor 101 in accordance with administration instructions. In some instances, a source of motion may be introduced between the skin site 126 and collection membrane 122 to provide a similar effect. Such motion could be introduced either through physical structures designed to move the platen 120 and collection membrane 122 or through the imposition of collection protocols that make motion part of the usage procedure for the sensor 101. In one embodiment, motion is effected before or after imaging of the skin site 126, although such separation is not necessary in all embodiments since the motion may be sufficiently slight that it does not appreciably affect the quality of collected images. In one embodiment, the motion may be driven by transducers such as ultrasonic transducers, sonic transducers, piezoelectric actuators, and the like. In other embodiments, sources of electromagnetic radiation such as ultraviolet light or electric fields may be introduced to accelerate the desquamation process.

Another nonchemical mechanism that may be used in other embodiments includes a mechanism for generating airflow over the skin site, perhaps coupled with a collector filter to gather cells thereby removed from the skin site 126. Such airflow could be generated with fans positioned near the collection membrane 122 or with a source of suction. Suction may also be used more directly in other instances to remove cells through the action of the suction itself. In one embodiment, the skin site is exposed to still or flowing water or other liquid, which may then be retrieved and filtered to extract skin cells.

In further embodiments, the membrane 122 comprises a slightly abrasive surface to promote dislodging of skin cells from the skin site. Such abrasive techniques may vary according to the structure of the collection membrane 122, which may provided with a roughened surface, or the addition of a material such as a mechanical exfoliant introduced between the skin and membrane, or may be implemented through the use of additional structures. For instance, an array of very fine needles may be disposed over the platen 120 so that they penetrate the collection membrane 122 and act to gather interstitial fluid when the skin site 126 is positioned on the collection membrane 122.

The action of any of these mechanisms may be further promoted when combined with another. For example, the use of fine needles or of an abrasive collection-membrane surface may be enhanced when motion is also used. The effectiveness of adhesive collection mechanisms may be increased when combined with the use of heat or pressure. Chemical mechanisms need not operate in isolation, and even multiple chemical methods may be used simultaneously, such as in embodiments where the collection membrane 122 is coated with a combination of substances to promote adhesion, secretion from the skin site, and the sloughing of skin cells. Other mechanisms not mentioned specifically herein are also understood to be within the scope of the invention, whether they are used alone or in combination with some of the methods described in detail.

The sensor layout and components may advantageously be selected to minimize the direct reflection of the illumination into the detection optics 115. In one embodiment, such direct reflections are reduced by relatively orienting the illumination subsystem 123 and detection subsystem 125 such that the amount of directly reflected light detected is minimized. For instance, the optical axes of the illumination subsystem 123 and the detection subsystem 125 may be placed at angles such that a mirror placed on the platen 120 does not direct an appreciable amount of illumination into the detection subsystem 125. In addition, the optical axes of the illumination and detection subsystems 123 and 125 may be placed at angles relative to the platen 120 such that the angular acceptance of both subsystems is less than the critical angle of the system; such a configuration avoids appreciable effects due to TIR between the platen 120 and the skin site 126.

An alternative mechanism for reducing the directly reflected light makes use of optical polarizers. Both linear and circular polarizers can be employed advantageously to make the optical measurement more sensitive to certain skin depths, as known to one familiar in the art. In the embodiment illustrated by FIG. 1, the illumination light is polarized by linear polarizer 107. The detection subsystem 125 may then also include a linear polarizer 111 that is arranged with its optical axis substantially orthogonal to the illumination polarizer 107. In this way, light must undergo multiple scattering events to significantly change its state of polarization. Such events occur when the light penetrates the surface of the skin and is scattered back to the detection subsystem 125 after many scatter events. In this way, surface reflections at the interface with the skin site 126 are reduced.

The detection subsystem 125 may incorporate detection optics that comprise lenses, mirrors, and/or other optical elements that form an image of the region near the platen 120 onto the camera 117. The detection optics 125 may also comprise a scanning mechanism (not shown) to relay portions of the platen region onto the camera 117 in sequence. The detection subsystem 125 may be configured to be sensitive to light that has penetrated the surface of the skin and undergone optical scattering within the skin and/or underlying tissue before exiting the skin. In some cases, the light source 103 may be a broadband light source used without a spectral filter 109 in the illumination subsystem 123. Instead, a color filter array comprising a microarray of different bandpass filters may be incorporated directly onto the image array of the camera 117. A specific common color filter array that is present on many color imaging chips is a Bayer filter, which describes an arrangement of red, green, and blue passband filters, as known to those of skill in the art.

As discussed above, it may be advantageous to measure images taken under different polarization conditions. An example of a way to do this can be seen by referring to the two illumination subsystems 123a and 123b. In this embodiment, one illumination subsystem 123a incorporates a linear polarizer 107a in a crossed polarization condition relative to the detection polarizer 111. A second illumination subsystem 123b omits the linear polarizer 107b. In this configuration, a first image may be collected with the polarized illumination subsystem 123a, which will substantially represent optical scatter and other effects below the surface of the skin 319. A second image may then be collected with the unpolarized illumination subsystem 123b. Although a polarizer 111 is in place in the detection subsystem 125, the illumination light in this second image is not polarized and the resulting image will be due in part to surface reflections and very shallow scattering of light as well as from deeper scattering of light from the skin site 126. The combination of the two images may be used to provide additional useful information.

The illumination subsystem 123 and detection subsystem 125 may be configured to operate in a variety of optical regimes and at a variety of wavelengths. One embodiment uses light sources 103 that emit light substantially in the region of 400-1000 nm; in this case, the camera 117 may be based on silicon detector elements or other detector material known to those of skill in the art as sensitive to light at such wavelengths. In another embodiment, the light sources may emit radiation at wavelengths that include the near-infrared regime of 1.0-2.5 μm, in which case the camera 117 may comprise elements made from InGaAs, InSb, PbS, MCT, and other materials known to those of skill in the art as sensitive to light at such wavelengths.

In a further alternative, the illumination subsystem 123 comprises a broadband illumination subsystem and the detection subsystem 125 comprises imaging optics 115 and 119, a crossed linear polarizer 111, and a dispersive optical element 113. The dispersive optical element 113 may comprise a one- or two-dimensional grating, which may be transmissive or reflective, a prism, or any other optical component known in the art to cause a deviation of the path of light as a function of the light's wavelength. In the illustrated embodiment, the first imaging optics 119 acts to collimate light reflected from the skin site 619 for transmission through the crossed linear polarizer 111 and dispersive element 113. Spectral components of the light are angularly separated by the dispersive element 113 and are separately focused by the second imaging optics 115 onto the camera 117.

Another example of a suitable system is illustrated schematically with FIG. 1B for an embodiment that takes the form of an optical topographic sensor. As used herein, the phrase "optical topographic imaging" is not intended to be limiting. Indeed, the techniques and methodologies disclosed herein allow the extraction not only of topographic features but also other features of the imaged portion of the skin site that include reflectance features such as albedo and chromaticity, among others. In some instances, only the topographical information is used, but in other cases, a combination of topographic and other information is used. The drawing is highly schematic and is intended to illustrate the direct collection of multiple images taken at different illumination angles. In actual implementation, the different components shown in the drawing may be packaged into a single unit, with the drawing showing internal components of such a package.

The optical topographic sensor 130 comprises a plurality of light sources 134, each of which may be implemented as a substantially monochromatic light source using, for example, light-emitting devices ("LEDs") or laser diodes ("LDs"). Substantially monochromatic light may alternatively be generated using narrowband or broadband sources with appropriate optical-filter elements. Light from the sources 134 is directed to platen 142 that includes an overlying membrane as described above for the collection of cells when in contact with a skin site 140. The platen and membrane are at least partially transparent at the wavelength of the sources so that the skin site 140 may be illuminated and imaged with a camera 144. "Direct" collection of the images means that each of the images collected by the camera 144 is not limited to areas in which the skin site 140 is in optical contact, but may additionally include other areas of the skin site 140.

The light sources 134 are generally disposed to provide different angles of illumination and may, in some embodiments, be disposed circumferentially about a circle in a plane substantially parallel to the platen 142. In some instances, the sources 134 are disposed uniformly about the circle, i.e. in an azimuthally uniform distribution, but in other embodiments the dispositions may be nonuniform. When the sources 134 are disposed about the entirety of the circle, they may provide 360° interrogation of the skin site 140, but in other embodiments, only a portion of a circle might be provided with coverage, such as when the positions of the light sources 134 define a semicircle.

It is generally expected that the optical topographic sensor 130 be deployed under circumstances in which the camera 144 and skin site 140 are substantially stationary relative to each other, and in which the light sources are illuminated in a fixed sequence during imaging. The same imaging principles may be applied in other circumstances where relative motion between the skin site 140 and the camera 144 may be mathematically accounted for. Because the arrangement has a fixed geometry, particular sensors 130 may be calibrated using a variety of techniques that include analysis of previously acquired optical-topographic-imaging data. Such calibrations may then advantageously be applied to future measurements with the particular sensor. This is related to the ability of the imaging techniques to make use of machine-learning algorithms and is described further in copending, commonly assigned U.S. Prov. Pat. Appl. No. 61/473,860, entitled "OPTICAL TOPOGRAPHIC IMAGING," filed Apr. 11, 2011 by Horst Arnold Mueller et al., the entire disclosure of which is herein incorporated by reference for all purposes. In particular, because the device 130 is used generally to image a known and limited class of samples that have similar optical characteristics, namely fingerprints, previously collected datasets may be used to derive rules, coefficients, features, relationships, and other aspects of the imaging. These various quantifications can be analyzed and refined using machine-learning algorithms to enhance the analysis of different fingerprints.

The relative position of the light sources 134 with the platen 142 provides for near-field illumination of the skin site 140. This may cause the illumination intensity and the illumination angle to vary across the object plane as defined by the platen 142. Illumination intensity variation may be corrected through flat-fielding if desired, and it is believed that variation of illumination angle may be partially compensated for by symmetric system design.

It is noted that the direct-imaging structures illustrated in FIGS. 1A and 1B do not require full contact of the skin site with either the collection membrane or platen since the direct imaging still enables imaging of those portions that are not in contact. This allows greater collection of data than conventional fingerprint imagers, particularly of those skin-site surfaces that may have natural curvatures that renders them unnatural to place in contact with a surface. One example is the naturally concave shape of the palm, and there are other skin-site surfaces that are similarly curved.

Figure 2:
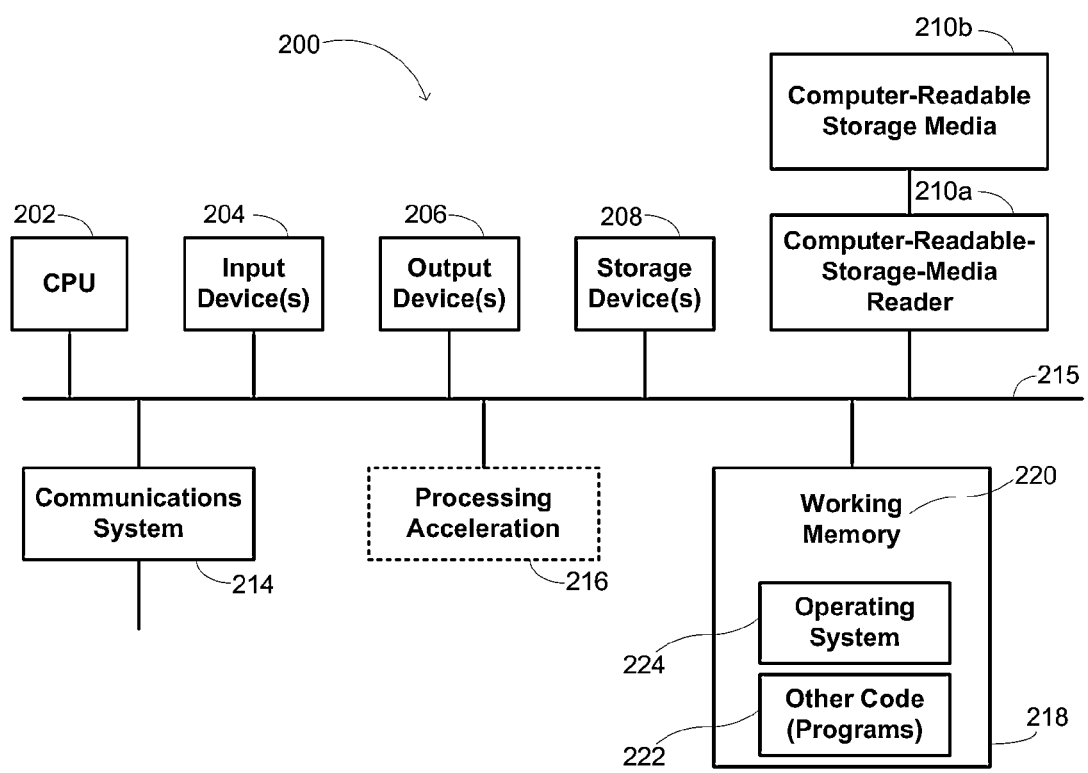
FIG. 2 is a schematic representation of a computational unit that may be used to manage functionality of the multispectral biometric sensor or of the optical topographic imaging device shown in FIG. 1A or 1B.

With both the structure of the multispectral sensor of FIG. 1A and of the optical topographic sensor of FIG. 1B, a computational unit is provided in communication with the camera and with the light sources, denoted by reference number 128 in FIG. 1A and by reference number 144 in FIG. 1B. The computational unit is configured to operate the respective sensor and to analyze collected data. FIG. 2 provides a schematic illustration of the computational unit, which is designated generically by reference number 200. It may form part of the respective device itself, packaged with the other elements, or may be provided separately. It is shown comprised of hardware elements that are electrically coupled via bus 215. The hardware elements include a processor 202, an input device 204, an output device 206, a storage device 208, a computer-readable storage media reader 210a, a communications system 214, a processing acceleration unit 216 such as a DSP or special-purpose processor, and a memory 218. The computer-readable storage media reader 210a is further connected to a computer-readable storage medium 210b, the combination comprehensively representing remote, local, fixed, and/or removable storage devices plus storage media for temporarily and/or more permanently containing computer-readable information. The communications system 214 may comprise a wired, wireless, modem, and/or other type of interfacing connection and permits data to be exchanged with external devices.

The computational unit 200 also comprises software elements, shown as being currently located within working memory 220, including an operating system 224 and other code 222, such as a program designed to implement methods of the invention. It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed.

Figure 3:
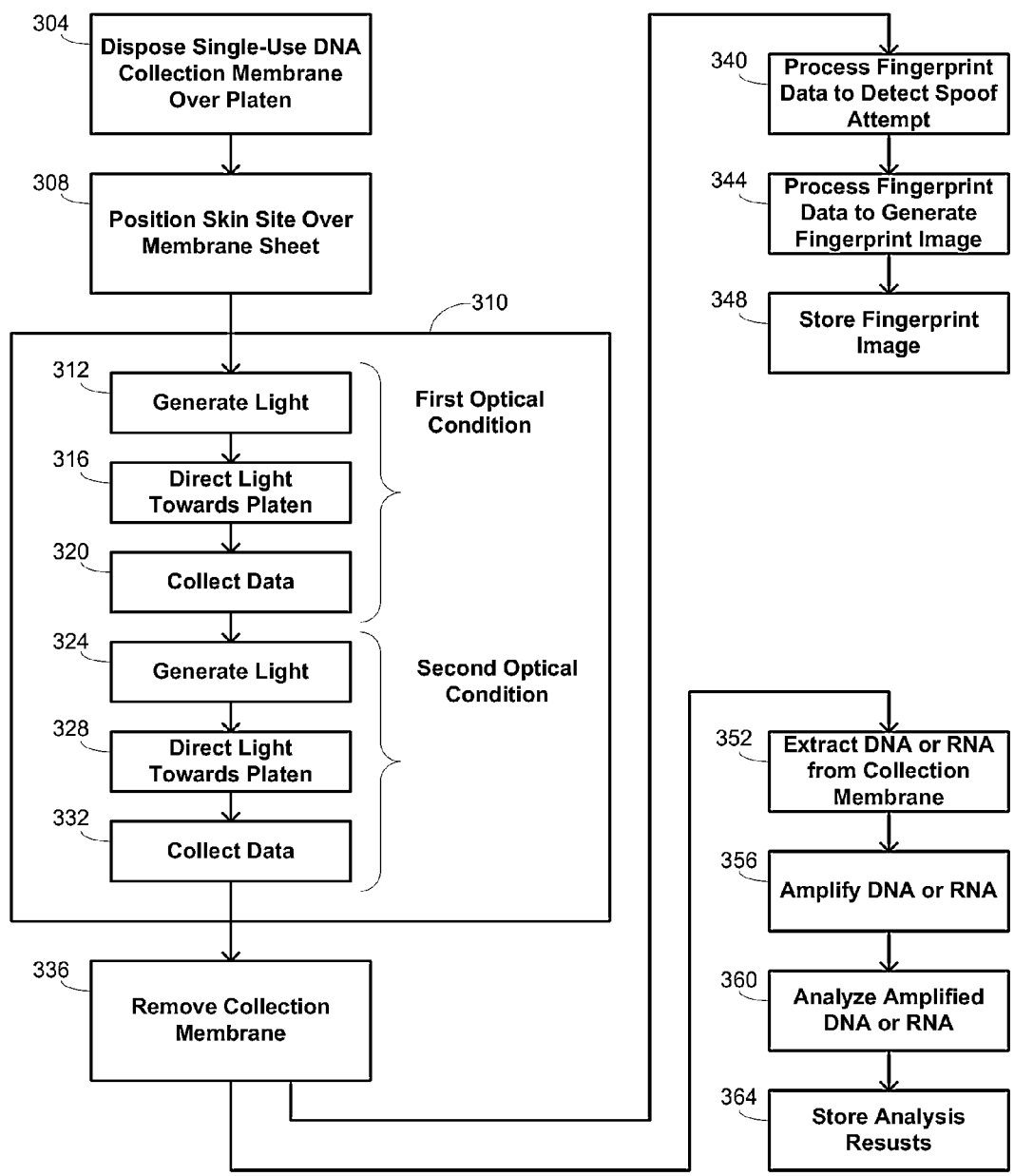
FIG. 3 is a flow diagram summarizing methods of the invention for simultaneous collection of fingerprint and genetic data as used in embodiments of the invention.

Ways in which data may be collected with the structures of FIG. 1A or 1B are summarized with the flow diagram of FIG. 3. While the flow diagram sets forth a number of steps that may be performed and provides an illustrative ordering of those steps, this is not intended to be limiting. In other embodiments, some of the steps explicitly shown might be omitted, other steps not explicitly shown may also be performed, and the ordering of the steps may be changed. The method described in connection with FIG. 3 may be performed with a variety of direct-image fingerprint sensors, including not only those shown in FIG. 1A or 1B, but also other structures, such as those shown and described in commonly assigned U.S. Pat. No. 7,460,696, the entire disclosure of which is incorporated herein by reference, as well as others.

At block 304, a single-use membrane like that described above (e.g., membrane 122 of FIG. 1A) is disposed over a platen (e.g., platen 122) of the sensor (e.g., sensor 101). The membrane is preferably sterile so that cells collected by the membrane (e.g., on first side 127 of membrane 122 when the skin site 126 is in the first position of FIG. 1A), whether it be because of its inclusion of an adhesive or abrasive surface or otherwise, are known to be cells of the person whose fingerprint is to be collected. This confidence is further increased by adoption of a protocol intended to ensure that the membrane is a single-use membrane so that the risk of contamination by other cells is minimized. Collection of both fingerprint information and cells is enabled by the positioning of a person's skin site over the collection membrane at block 308.

At block 310, direct-image fingerprint data are collected. For purposes of illustration, the drawing expands block 310 to illustrate the collection of multispectral data, but it will be understood that other types of direct-image fingerprint data may alternatively be collected, including optical-topographic fingerprint data.

Within block 310, blocks 312-320 correspond generally to the collection of data under a first set of optical conditions, with light being generated with a light source at block 312 and directed to the platen surface at block 316 to provide illumination of the skin site through the collection membrane. As indicated at block 320, data then collected with light from the skin site.

Blocks 324-332 similarly correspond generally to the collection of second data under a second set of optical conditions different from the first set of optical, but otherwise replicating the steps in blocks 312-320. The first and second data may be collected sequentially or substantially simultaneously in different embodiments, but are collected during a single session with the sensor. The first and second sets of optical conditions may differ in any number of respects, including the wavelength of interrogation light, the angle of incidence of the interrogation light on the skin site, the receipt angle of light directed to the camera, the polarization conditions, and others.

In some embodiments, the collection membrane may include a mark that may be imaged by the camera at the same time that a fingerprint image is acquired, with the mark having a position, size, and/or quality that prevents it from interfering significantly with the fingerprint image. For instance, such a mark might be located at the edge of the region imaged by the sensor. In this way, the fingerprint image, which may include an image of the marking, and the membrane with the associated genetic material may be identified as a pair. The marking may comprise a one-dimensional or two-dimensional barcode in some embodiments, or may comprise machine-readable lettering or other forms of machine-readable data.

The collection membrane is removed at block 336, enabling parallel fingerprint and genetic analyses to proceed, as indicated separately in the drawing. A variety of biometric analyses may be performed on the fingerprint data. For example, as indicated at block 340, the fingerprint data may be analyzed as part of a spoof-detection procedure. This generally involves a multispectral analysis being performed on the data collected at blocks 320 and 332 to compare measured multispectral properties with anticipated properties of living human skin or, in some cases, to compare it to the anticipated multispectral properties of a specific person. Any of several types of discriminant techniques may be used to perform spectral comparisons whereby spectral information is extracted from multispectral data by ignoring the spatial information while preserving the relationship of the optical properties observed across the different optical conditions. Several examples are described in detail in commonly assigned U.S. Pat. No. 6,560,352, the entire disclosure of which is incorporated herein by reference for all purposes. For instance, suitable discriminant techniques may include techniques based on Mahalanobis distances, spectral residual magnitudes, K-nearest-neighbor models, and other linear or nonlinear discriminant techniques. Multispectral imaging techniques as described herein may provide information on external friction ridge patterns of the skin site, internal friction ridge patterns, composition and position of other subsurface structures, spectral qualities of the skin site, the size and shape of the skin site, the texture of the skin site, and other features and statistical qualities that are distinct between human skin and various artificial materials and spoofing methods.

At block 344, the fingerprint data are processed to generate a fingerprint image that may be a composite image derived from the data collected under different optical conditions. Generally, there are one or more optical conditions that will produce a well-defined fingerprint image under most environmental and physiological conditions, assuming the skin site measured has well-defined ridge and valley features. For example, in the case where the finger is moist and in good optical contact with the platen, direct-imaging techniques remain as capable of producing high-quality, high-contrast images as more conventional TIR imaging. If the skin is particularly dry and/or not well coupled to the platen, direct imaging methods tend to produce images of significantly higher quality than TIR imaging techniques. In addition, the inventor has observed that different wavelengths often define certain features such as fingerprint patterns or scars, better than other wavelengths in certain portions of the image field and/or for certain skin sites. Also, wavelengths less than approximately 580 nm tend to produce features that are "blotchy" due to being sensitive to blood distributions in the skin. However, the sensitivity to blood can produce good quality fingerprint patterns in certain cases. Conversely, wavelengths longer than approximately 580 nm tend to produce more homogeneous representations of the fingerprint and other features of the skin site. The inventor has also observed that certain polarization conditions provide good fingerprint features only under certain conditions. For example, random polarization or parallel polarization configurations tend to show well-defined surface features in those cases where the finger is not in good optical contact with the platen. Generally, however, the features produced by these polarization configurations are less well-defined when there is good optical coupling between the skin site and the platen. The cross-polarized configuration appears to be much less sensitive to such coupling variations.

To produce a useable fingerprint biometric over a wide variety of conditions, the fingerprint data collected under the plurality of optical conditions may be combined in some way. For example, each of the sets of data for a single illumination session taken under distinct optical conditions may be processed separately to enhance fingerprint patterns using band-pass filters, median filters, Fourier filtering, Gabor filters, histogram equalization, and other linear and nonlinear enhancement techniques known in the art. The resulting enhanced images may then be combined in some way, such as by taking a simple average of the images. Another technique is to assess the fingerprint quality of each of the images using standard-deviation metrics and other methods known in the art, and just average together those images with sufficient quality, or to perform a weighted average across the images where the weighting is proportional to quality, etc. In some cases, the data from a single illumination session may be combined using photometric stereo techniques to produce a topographic image as well as an albedo or reflectance image.

After the fingerprint image has been generated at block 344, it may be stored, such as in the storage device 208 of the computational unit, at block 348.

In parallel or sequential with the generation of the fingerprint image, DNA or RNA (referred to collectively herein as "NA") may be extracted from the collection membrane at block 352 and amplified at block 356. Various methods are known in the art for NA extraction from cells collected by the collection membrane and for its amplification, and the invention may be practiced with any of a variety of such methods. Merely by way of example, in one embodiment the collection membrane is removed from the sensor and partially or entirely immersed in an extraction buffer that is then boiled, followed by alcohol precipitation of NA Inhibitors of polymerase chain reactions ("PCR") are removed by including mixed ion-exchange resins in the extraction buffer. PCR is a known technique for amplifying NA and may be used at block 356.

The number of cells that need to be collected in order to have reliable extraction and amplification is small, and in some embodiments comprises fewer than ten epidermal cells. The techniques of "low copy number DNA" and "touch DNA" may be applied to (epi)dermal cells, sebaceous cells, and other cells that may have been collected by the membrane when in contact with the skin site. These techniques operate in a manner similar to conventional PCR analysis, but with a greater number of amplification cycles so that enough NA is generated to perform the genetic analysis at block 360. The results of the analysis, which are preferably in a form that allows the identification of genetic anomalies, are stored at block 364 such as in the storage device 208 of the computational unit.

It is noted that direct imaging of the skin site solves many problems associated with attempts to collect NA simultaneously with fingerprint measurements that use TIR imaging because there are far fewer concerns about optical coupling. TIR imaging requires precise optical coupling in order to collect reliable fingerprint data, requiring that a collection membrane such as described above be positioned relatively precisely. By using direct imaging to collect fingerprint data, the methods of FIG. 3 are largely insensitive to positioning of the collection membrane, provided it is positioned so that it will contact some portion of the skin site during measurement so that cells may be collected.

Figure 4B:
FIGS. 4A and 4B provide a comparison of fingerprint images collected with different types of fingerprint imagers with the presence of an optically clear film.
Figure 4A:

This advantage may be better understood with reference to FIGS. 4A and 4B, which show the effect of placing a thin, optically clear film on a finger. In this illustration, the optically clear film was simply transparent tape. FIG. 4A shows the resulting TIR image, which includes a blank region at the locations where the tape is present. This is in marked contrast to the average direct image of FIG. 4B that was observed in the same set of multispectral measurements. In this case, the direct imaging used a cross-polarized configuration taken across multiple illumination wavelengths. As obvious from the drawings, the resulting direct images are able to see skin structure and other features that lie below a thin film even where the TIR images are not.

Figure 5:
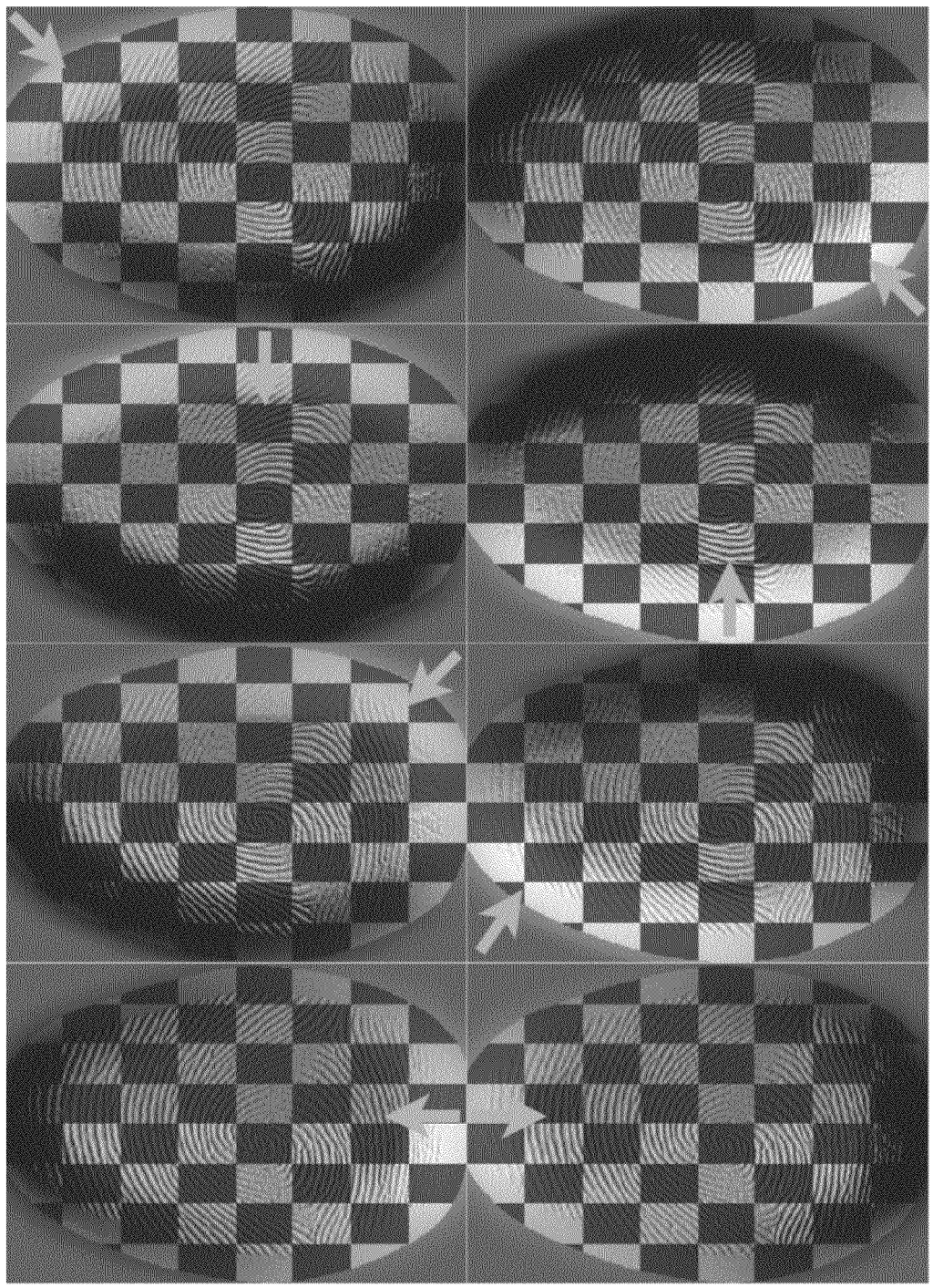
FIG. 5 provides a series of images that illustrate the effect of topographical features such as surface shape and reflectance when images of an object are collected at different illumination angles.

An illustration of effects used by the optical topographic sensor 130 of FIG. 1B is provided with FIG. 5, which shows the effect of illuminating a surface at different illumination angles. The drawing shows eight images of a test object illuminated at different illumination angles, with the object corresponding to a biometric fingerprint having a three-dimensional shape to which reflectance has been added to follow the surface, as illustrated by the checkered pattern. The different panels in the drawing correspond to images produced with different azimuth illumination directions for an elevation angle of 45° and an azimuth angle of 45°. The surface shape and reflectance cause different effects in the image as the illumination angle changes, allowing different kinds of information to be extracted.

Figure 6:
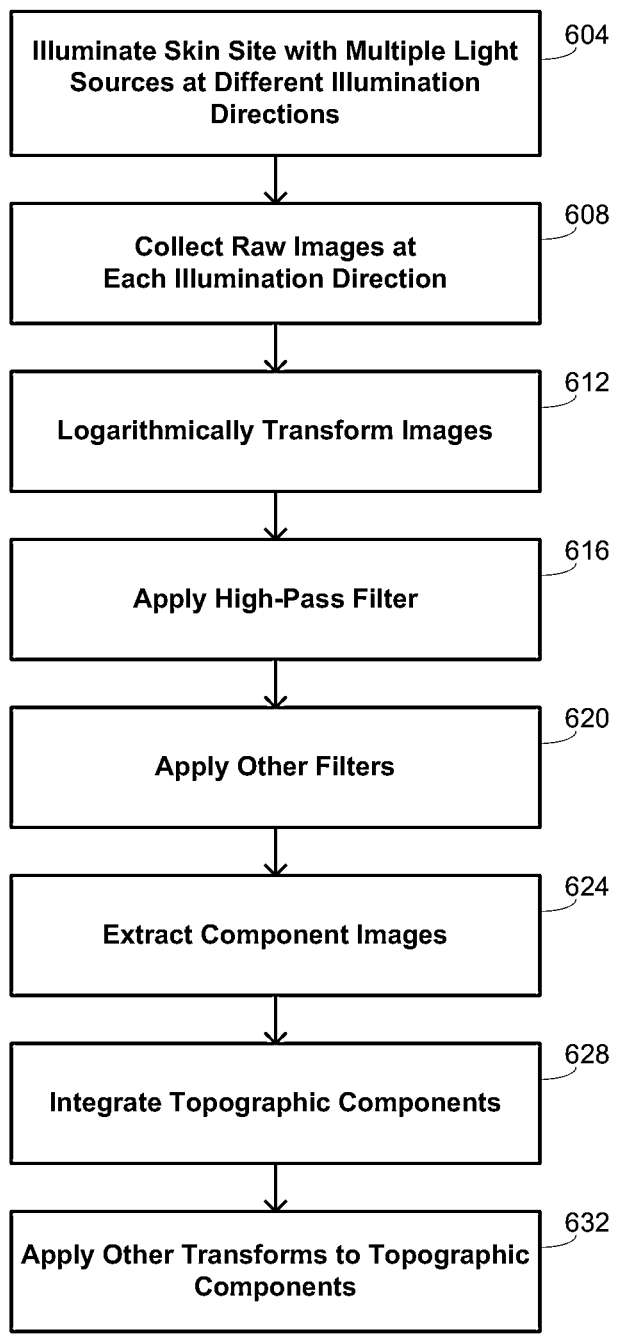
FIG. 6 is a flow diagram summarizing methods of applying topographic analysis to images collected with the optical topographic imaging device of FIG. 1B.

A methodology for extracting these different kinds of information is illustrated with the flow diagram of FIG. 6. Again, the specification of specific steps in a specific order in the drawing is not intended to be limiting since some steps may be omitted, some steps may be added, and steps may be performed in an order different than that shown. The ordering of the steps in the exemplary embodiment at times advantageously exploits physically geometrical aspects of the sensor structure 130 shown in FIG. 1B to simplify processing.

The methodology begins at block 604 by illuminating the skin site using the multiple light sources of the optical topographic sensor at different illumination directions. The illumination by the different sources may be sequential, particularly in instances where the light sources are substantially monochromatic at the same wavelength, to obtain separate images at different directions like shown in FIG. 5. Raw images are thus collected at each illumination direction at block 608, forming the raw image dataset from which information about the skin site is to be extracted.

At block 612, a logarithmic transformation may be applied to the raw image data, thereby converting the raw intensity data to pseudo-absorbance. Different embodiments may use any logarithmic base for the transformation, including both common and natural logarithms. Such a logarithmic transformation to pseudo-absorbance advantageously converts certain multiplicative optical effects to additive optical effects. For example, the albedo, defined as the dimensionless ratio of reflected intensity to incident intensity, combines multiplicatively in raw data space, but combines additively in logarithmic data space.

At block 616, a high-pass filter is applied. Such application advantageously sharpens the image by retaining high-frequency information while reducing low-frequency information. Examples of high-pass filters that may be applied include Laplacian filters, Laplacian-of-Gaussian filters, Difference-of-Gaussian filters, and others. Application of the high-pass filter may sometimes be delayed to later in the process shown in FIG. 6. For example, gradient functions or normal vectors may have filtering applied to enforce planarity.

At block 620, other filters may also be applied. In some embodiments, different processing is beneficially applied according to each different illumination condition, one example of which is scatter correction. For instance, scatter correction may be implemented by recognizing that a portion of light reflected from skin comes from bulk subsurface scattering. At wavelengths in the silicon region, such scattering is anisotropic, with the scattering favoring a forwards direction along the incident illumination line. This scattering anisotropy causes the raw images to include a characteristic blur that varies according to the illumination angle. The effect may be mitigated by applying an appropriate filter such as a deconvolution with an appropriate kernel to the raw images. Each raw image may thus be processed with a kernel appropriate to the illumination condition.

Component images are extracted from the filtered images at block 624. The method of extraction depends on the particular components to be extracted. For example, the albedo may be extracted as a mean of the logarithmic intensities using a constant extraction factor.

Surface gradients that define topographic information may be extracted by using periodic factors defined according to system geometry. For example, in an embodiment where the light sources are distributed at constant elevation and uniformly in azimuth over a full 360° angular range, the extraction factor for the x-direction surface gradient $S_x$ may be sinusoidal and the extraction factor for the y-direction surface gradient $S_y$ may be the same in quadrature. The sense (i.e. clockwise or counterclockwise) and the phase of the extraction factors match the sensor configuration. Definition of other extraction factors according to system geometry will be evident to those of skill in the art, and may include nonsinusoidal factors in some embodiments.

In some embodiments, the extraction factors used to generate the surface gradients $S_x$ and $S_y$ are selected to reduce sensitivity to DC light. This not only reduces the effect of DC ambient lighting around the sensor on the extraction factors, but also reduces the influence of albedo on the surface-gradient extraction factors. In still other embodiments, the factors also have reduced sensitivity to other nonsynchronous illumination changes, which enhances discrimination against ambient light that fluctuates during sampling. This may be an issue, for example, when the sensor is deployed in an environment illuminated with fluorescent lighting.

There are multiple ways in which the extraction factors may be selected to meet these different criteria. In some embodiments, extraction factors are defined by a human being to accommodate most commonly expected light conditions in environments where the sensors are to be deployed. In other embodiments, sensors may be more specifically tailored by having different sensors that are configured to be suitable for broadly defined categories of lighting conditions: for instance, one configuration of device might be marketed as being suitable for outdoor daytime use, with extraction factors optimized to accommodate bright sunlight and the presence of certain levels of cloud cover; another configuration might be marketed as being suitable for office environments, with extraction factors optimized for fluorescent lighting conditions; and another configuration might be marketed as suitable for dim-light use, with extraction factors that are substantially sinusoidal. In other instances, extraction factors may be defined very specifically for a particular environment by having a human being examine the deployment environment, perhaps performing optical tests of the environment, and deriving appropriate extraction factors.

In still other embodiments, machine-learning techniques may be used to have the sensor develop extraction factors that are tailored to the deployment environment according to specific data collected while deployed in that environment.

At block 628 of FIG. 6, the extracted topographic components are integrated to generate the topographic image by integrating the surface gradients $S_x$ and $S_y$. The integration is generally carried out numerically using any of a variety of known integration methods such as the Frankot-Chellappa method, methods using shapelets, and the like.

Once the topographic image is generated, other transforms may be applied at block 632, particularly to further modify the resulting topographic image and render it more suitable for subsequent processing. In particular embodiments, the image is modified to change the contrast, to reduce artifacts resulting from specular light, to binarize the image, and the like. Similar to the machine refinement of the topography extraction factors, such transformations may be developed with machine-learning techniques applied to data collected while the sensor is deployed so that they may be applied to current and future data.

In other embodiments, standard photometric stereo methods may be used to process the set of images shown in FIG. 5. Such methods produce estimates of surface topography and albedo under various assumptions about the optical characteristics of the object.

Figure 7A:
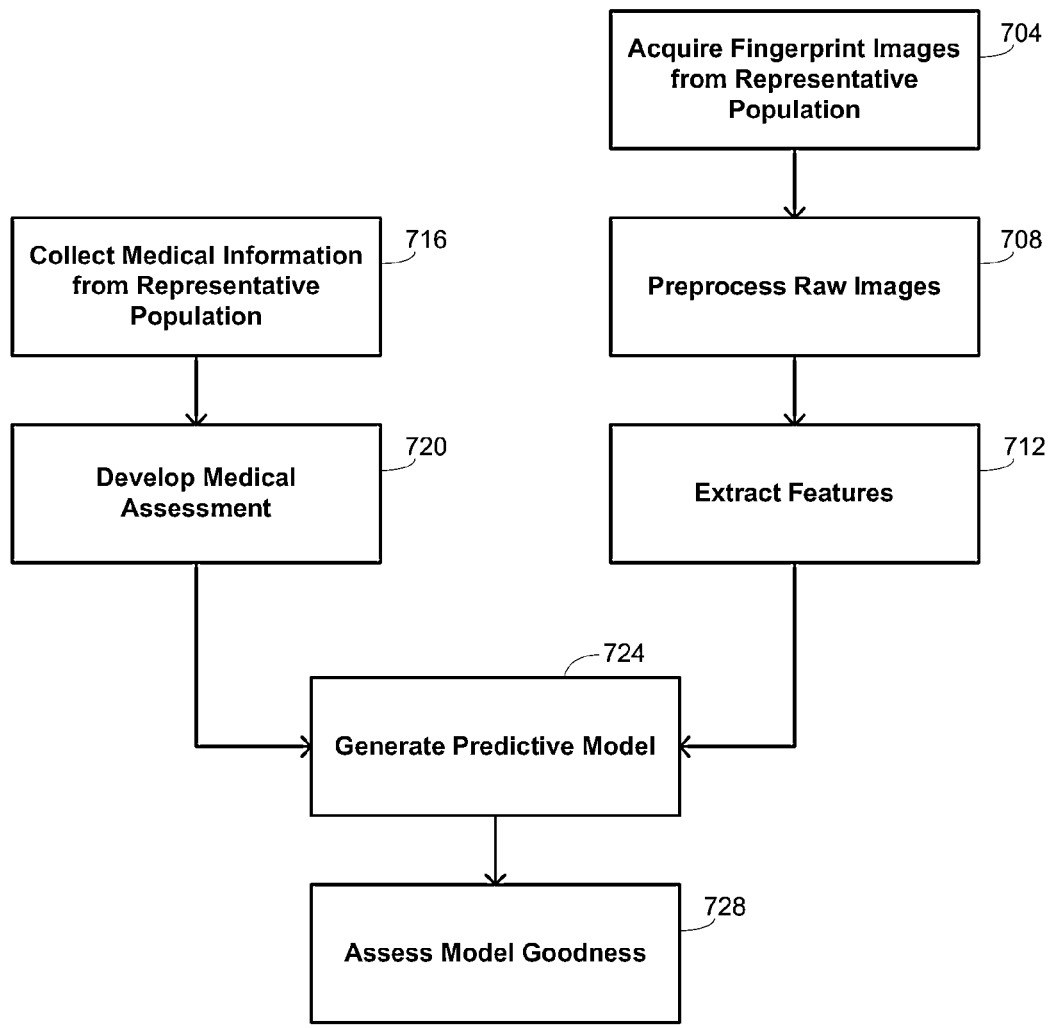
FIGS. 7A and 7B are flow diagrams summarizing methods of using a biometric sensor in performing correlations with genetic markers.
Figure 7B:
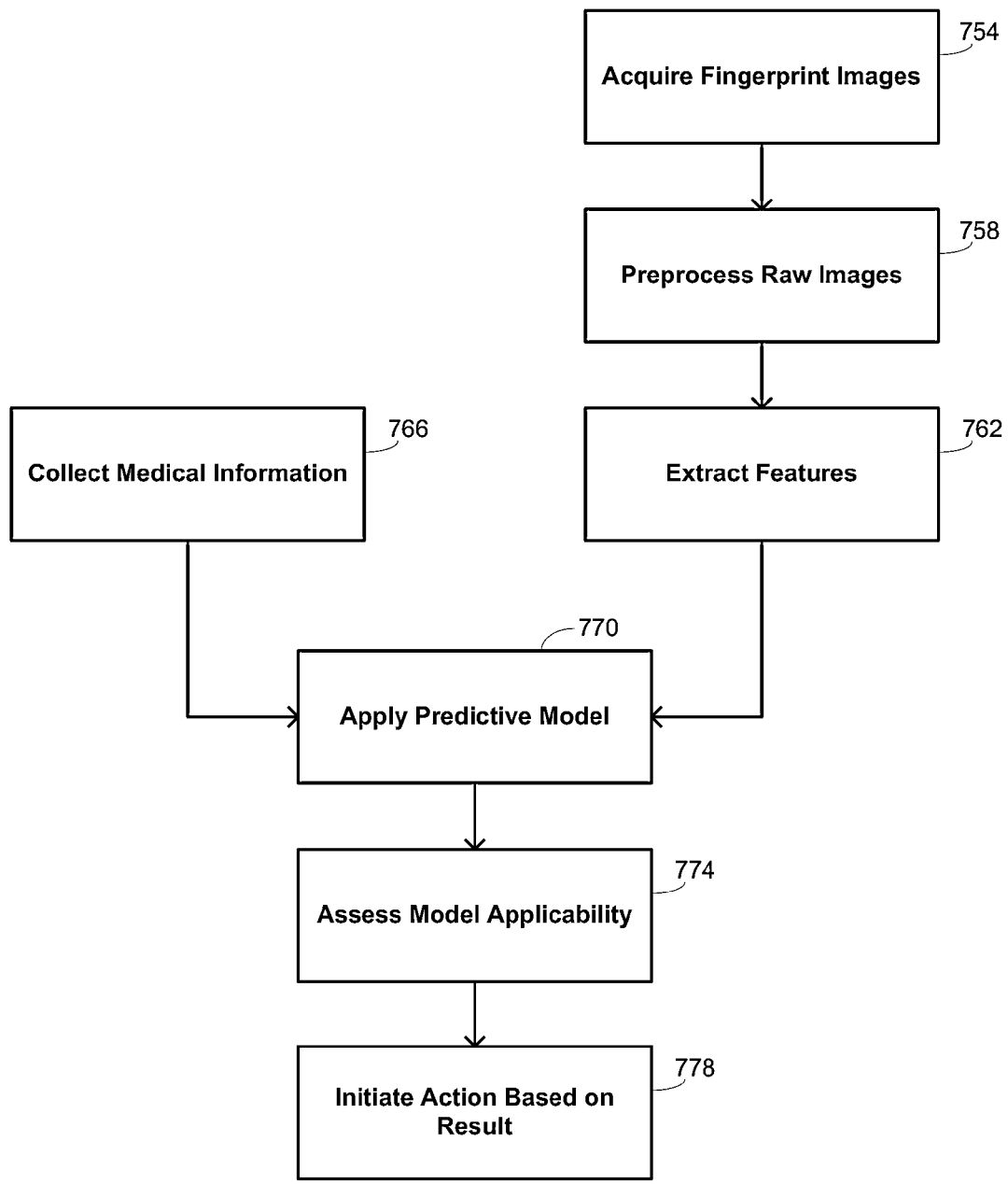

Regardless of which type of sensor is used, including TIR sensors, multispectral sensors, optical topographic sensors, semiconductor sensors (capacitance, radio-frequency, etc.), paper-and-ink fingerprints, direct photographs of fingerprints, and the collection of latent fingerprints), similar methods may be used as illustrated in FIGS. 7A and 7B to establish and use correlations between fingerprint features and genetic markers. Importantly, the invention is not limited to any particular scheme for classification of fingerprints, but instead uses generalized image features, which may be derived feature information through machine learning that is more parsimonious, comprehensive, sensitive, and reliably correlated with genetic markers. In particular, conventional fingerprint classification schemes like the Roscher system, the Juan Vucetich system, and the Henry classification system generally rely on the identification of specific, pre-established patterns such as arches, loops, and whorls. This is true even in those classification schemes that break down such patterns ever further by distinguishing such features as arches as plain or tented arches, loops as radial or ulnar, or whorls as plain, accidental, double-look whorls, composite, or central-pocket, etc. Instead, embodiments of the invention impose no preconceived classification scheme on the data, allowing the machine-learning process to extract those factors with the highest reliability in establishing genetic-marker correlations.

Thus, FIG. 7A illustrates a calibration procedure according to the present invention. After fingerprints are acquired from a representative population at block 704, they may be preprocessed at block 708. Preprocessing methods include logarithmic and other transformations, gamma correction, contrast enhancement, noise filtering, background removal, color adjustment, and a variety of other such functions. Alternatively, in the case of certain raw-image sets collected according to embodiments of the invention, the raw images may be combined in some manner to produce one or more composite images. For example, a set of raw images collected with an optical topographic sensor may be processed to produce an image that estimates the surface topography of the fingerprint as well as an image that indicates the reflectance characteristics of the fingerprint. Either or both of these images, or values derived therefrom, may be used in subsequent steps.

The preprocessed images and/or the raw images are then analyzed to determine and quantify their characteristics. In particular, the presence, degree, and location of image features in the fingerprint images may be quantified ("extracted") as indicated at block 712. The term "features" as used herein refers to the specific mathematical characteristics being quantified and "feature magnitude" refers to the quantity of a particular feature. The feature magnitude may be a single number that describes the entire image (such as skin tone), or may comprise a set of numbers that vary across each image (such as complex wavelet coefficients). Features that are quantified may be based on methods and analysis performed for a variety of tasks in machine vision and pattern recognition including, but not limited to, any of the following: wavelet decomposition; Fourier transform; histogram of oriented gradients; scale-invariant feature transform; structure tensor elements; Hessian elements; multiscale analysis, including characterization of ridge, edges, and extrema; Laplacian of Gaussian filters; Gabor filters, principal components; independent components; chromaticity; gray-level intensities and intensity histogram; gray-level correlation values; fractal dimension; measures of flow characteristics (laminar, turbulent, rotational, curl, etc.); and the presence, location, and type of salient points based on flow characteristics.

For each person in the representative population from whom fingerprint images are collected, applicable medical information is also collected at block 716. In particular, analysis of DNA, RNA, and/or proteins may be performed. Such material may be collected using "touch techniques" described in more detail above, or may be derived from blood samples, tissue samples, and other methods known in the art. In addition or alternatively, other medical assessments may be made and recorded based on a variety of medical tests, medical histories (including family histories), medical interviews, and other methods and information known in the art.

Based on the medical data acquired, a medical assessment is made at block 720. Such a medical assessment may comprise a diagnosis or other type of assessment, and may be made by a trained professional, a team of professionals, or may be the result of an automated analysis of the pertinent medical information by an expert system of some kind. The medical assessment may be made of the absence, presence, and/or severity of a particular condition, including a genetic condition. Alternatively, the medical assessment may provide an indication of the degree of risk that an individual with a particular set of medical characteristics may express a certain medical condition at a later time.

The collection, analysis, and accumulation of such paired information (fingerprint feature magnitudes and medical diagnosis) is preferably performed far a large and representative population of people. In particular, such a calibration population should include a statistically meaningful number of people with and without the medical condition or conditions being targeted, as well as differing degrees of severity, duration, risk, or other salient characteristics relative to the modeling performed in the next step.

The medical information for a representative population and the feature magnitudes derived from corresponding fingerprint images may be used together to construct a predictive model at block 724. In particular, the fingerprint feature magnitudes may be used as the predictors and the medical diagnosis may be used as the response variable, and the model attempts to relate the two types of data. In some cases, supplemental medical information derived from medical interviews such as age, sex, ethnicity, family history, and/or other such data may be included with the image features as predictors in the model. Other supplemental information may be used as predictors as well, including time of day, temperature, location, equipment type, and other similar parameters. Such a model may be a regression model or a classification model. Regression models may be best suited to a continuous variable such as the risk of acquiring a particular genetic condition or the severity of such a condition. Classification models may be better suited to "yes or no" decisions, or to classifying the condition into a discrete number of variants. In either case, a variety of data-driven analytic methods may be employed to establish the model, including: neural networks, classification and regression trees, ensemble models (including decision trees), linear and nonlinear discriminant analysis, support vector machines, principal-component regression, partial least squares, and multivariate regression. It is generally expected that the reliability of the model will increase with the size of the representative population, particularly if that population has sufficient diversity to enable identification of a large number of potential fingerprint features.

Once a model is constructed, it may be informative to assess the goodness of the model at block 728. One manner in which the goodness can be determined (as well as a method of setting certain model parameters) is to use a cross-validation procedure in which a portion of the calibration data may be held out from the modeling process. The model that is then generated may be applied to the data not used for modeling to determine how well the model generalizes or applies to unmodeled data. This process may be repeated a certain number of times with different data held out and the results aggregated. In so doing, a somewhat representative assessment of the model performance may be made.

FIG. 7B illustrates methods by which predictions or screenings may be performed in accordance with the invention. For prediction, acquisition of the raw fingerprint images at block 754, preprocessing at block 758, and feature extraction at block 762 may be performed in a manner similar to the same processes performed during calibration. It is preferred that these steps be conducted in a manner as similar to the calibration as practical. In addition, in embodiments where medical information or other supplemental information is used as a predictor, such information is also gathered at block 766. The results of the feature extraction and the supplemental predictor information (if any) are then provided to the previously built model at block 770. It then produces an estimate of the modeled response variable(s).

In some embodiments, it is desirable to determine the applicability of the model to the data on which it is being applied at block 770. For example, in the case of principal-component regression, partial least squares, and other similar techniques, outlier metrics such as Mahalanobis Distance and residual magnitudes may be calculated to determine whether the data used to generate the present prediction are similar to the data used to generate the model. Other metrics and methods may also be used to determine the consistency of the model data with the prediction data. In cases where the two datasets are inconsistent, the prediction result may be canceled or given less weight when a follow-up action is determined. In other cases where the inconsistency might be due to a measurement error of some kind (such as movement of a finger during image acquisition, presentation of the wrong finger or wrong hand to the sensor, and the like), the prediction data may be collected again and the prediction rerun.

Once an acceptable prediction is obtained, the result may be used to initiate an action at block 778. For example, in an embodiment of the present invention used as a prescreening device, the followup action may be either to conduct a separate medical test such as a genetic test (if the risk of a certain genetic condition is high) or not to conduct such a test (if the risk is determined to be low).

There are numerous applications in which such models may be used. In addition to being less invasive, fingerprint collection is less costly than blood-based genetic testing so that the method finds particularly advantageous application in environments where cost is a concern. For instance, physicians might use the method as a form of preliminary genetic screening that is followed by blood-based genetic testing only with those individuals identified as having a high risk of genetic anomaly. Currently, many countries routinely require the acquisition of footprints from newborns, and these footprints can be subjected to this type of analysis as a cost-effective way of providing genetic screening. The methods of the invention also lend themselves to veterinary applications in which animal pawprints may be collected and analyzed.

It is also noted that the techniques of the invention may be applied to other phenotypical traits in addition to fingerprints. For example, similar measurements of the iris may be made and correlated with genetic markers in alternative embodiments, recognizing the potential for different phenotypes to have stronger or weaker correlates with genetic markers in different species.

Figure 8:
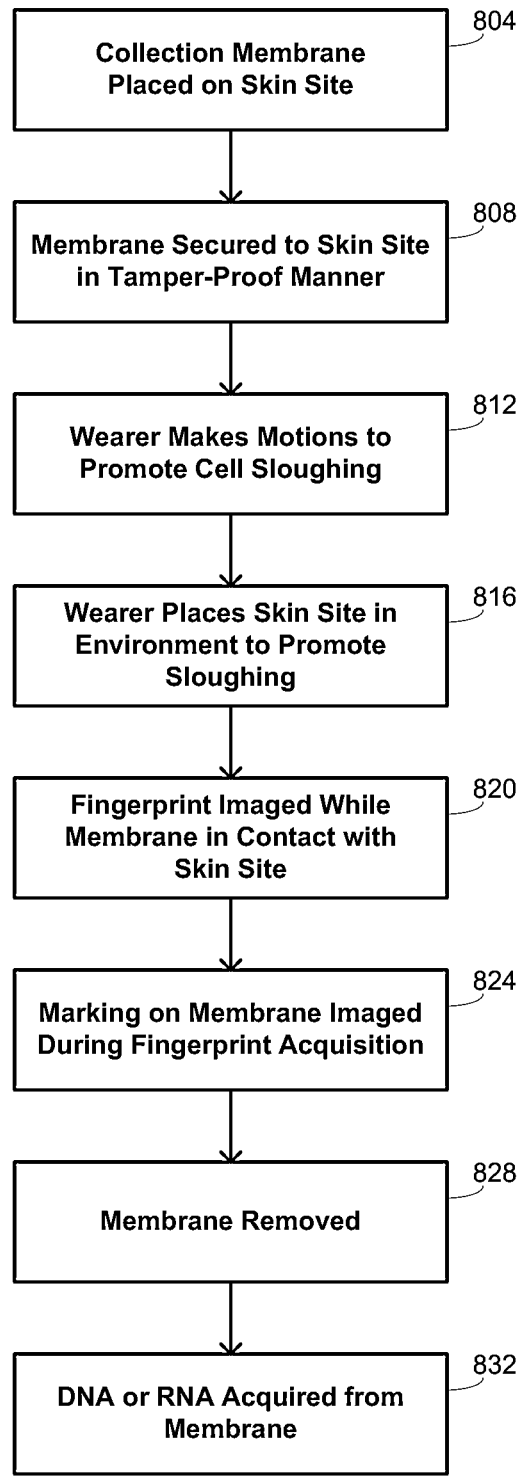
FIG. 8 is a flow diagram summarizing methods where a collection membrane is placed on a skin site.

FIG. 8 is a flow diagram summarizing embodiments of the invention in which a collection membrane is placed on a skin site of the individual being screened, rather than being disposed as part of the sensor. Such embodiments may be used under a variety of circumstances, but are of particular utility in instances where collected cellular samples may otherwise be of insufficient quality or quantity for a reliable genetic analysis. Such inadequate sampling might occur even if the membrane that is in contact with the fingers during imaging is pretreated with adhesives, abrasives, chemicals with affinity for skin cells, or the like. As known in the art, skin sloughing occurs at some rate such that more cells are sloughed over larger skin areas over longer periods of time. In addition, skin sloughing is a function of environment, activity levels of the individual, and other such parameters. The embodiments illustrated with FIG. 8 provide larger collection areas and/or longer contact times between the individual's skin and the sample membrane. These embodiments also advantageously permit the skin site to be subjected to other actions that might be possible during the period of active imaging.

As indicated at block 804 of FIG. 8, the collection membrane in these embodiments is placed on the skin site, which might comprise a finger, plurality of fingers, the entire hand, or any any other of the skin sites identified specifically above. Such placement is more usually performed prior to fingerprint-image acquisition, but other embodiments might use such placement after fingerprint-image acquisition.

As part of placing the collection membrane on the skin site at block 804, additional measures may be taken to increase the reliability of acquiring cellular samples of sufficient quality and quantity. For instance, in one embodiment, the collection membrane is comprised by an adhesive strip that is substantially clear with respect to at least one of the wavelengths of light used for imaging. Placement of the collection membrane may accordingly comprise placing the membrane on a portion of skin, as illustrated in FIG. 4B, or wrapping the adhesive strip around a fingertip and/or other portions of the finger, hand, or other skin site being imaged. In another embodiment, the membrane is comprised by a glove, finger cot, or other covering of the sort.

In certain instances, the security of the procedure may be enhanced by securing the membrane to the skin site in a tamper-proof manner, as indicated at block 808. There are a variety of ways in which this may be accomplished in different embodiments, one of which is where the membrane is comprised by a glove or glove-shaped covering having a secure fitting that makes it difficult to remove without an appropriate tool and/or without leaving an identifiable mark. For instance, the glove, cot, adhesive strip, or other form of membrane may be designed to be one-time-use—only with an ability readily to discern whether the membrane was removed. This may be done in embodiments in which a portion of the membrane adheres to itself when fitted to a finger, hand, or other skin site; the adhered portion may be designed to tear in some way or to uncover security markings or other features when the membrane is removed.

Similar to embodiments described above in which a collection membrane applied within the sensor, the collection membrane in these embodiments may be treated in some way to promote sloughing, at least on those portions of the collection membrane to be contacted with the skin site. For example, in one embodiment, the collection membrane has an interior surface (i.e., at least part of the portion in contact with the skin site) that is treated with a chemical that has an affinity for skin cells. In another embodiment, the interior surface is treated with a chemical that promotes skin sloughing. In other embodiments, the interior surface of the collection membrane has an abrasive quality such that relative motion between the membrane and the skin promotes cell sloughing. The abrasive quality may arise from the texture of the membrane itself, may arise from an additive applied to the membrane during fabrication, may arise from an abrasive cream or ointment applied to the skin or to the membrane prior to placement of the membrane, or from other such instantiations. In still other embodiments, the interior surface of the collection membrane includes an adhesive that facilitates removal of skin cells from the wearer.

Blocks 816 and 820 provide examples of actions that may further be taken to increase the sloughing of skin cells. Block 816, for instance, indicates that the wearer is asked or required to make motions to promote the sloughing. Examples of such motions include repeated flexing of a gloved hand by making a first and then fully extending the fingers, although many other types of hand motions will be evident as alternatives. Such hand motions have the effect of facilitating perspiration and skin sloughing, and may be of even greater effect in such embodiments when combined with adhesives, chemicals, or abrasives since the movement will act synergistically with such other elements.

Block 820 indicates that the wearer is asked or required to place the skin site within an environment that promotes skin sloughing. This might be achieved, for instance, by having the wearer move his hand under a radiant lamp or by moving warm air over the skin site. It will be appreciated that such environmental effects might be achieved in combination with use of the imaging sensor, particularly by using those environmental effects described above. The mechanism by which environmental effects promote skin sloughing may vary. While in some cases, the principal effect will be to increase perspiration by having the wearer place the skin site in a warm environment, the warmth of the environment may also improve the action of the chemical, adhesive, or abrasive techniques described above depending on the specific modalities that are used.

At block 820, the fingerprint is placed on the imaging sensor and imaged as described in detail above. In one embodiment, the collection membrane comprises a unique marking that may be imaged substantially simultaneously with the fingerprint as indicated at block 824. Such a marking may advantageously be used for unique association of the fingerprint and the membrane by subsequent review of the image(s).

In is noted that there are further embodiments in which the collection membrane is provided to the skin site as a conformal coating, such as a latex or silicon coating. Such embodiments may advantageously be less sensitive to the optical properties of the membrane. In particular, while such a conformal coating may be transparent at at least one wavelength used by the sensor, it may alternatively be opaque and reflective, i.e. light is reflected from the surface of the coating rather than transported through or absorbed by the coating. In some such embodiments, the topography of the reflective conformal coating matches the skin topography with required precision. In such instances, the imaging techniques described above may be used to acquire a set of images that enables the topography of the reflective conformal coating to be reconstructed using photometric stereo or other techniques as described above. In some instances, a unique identifier such as a barcode, writing, or other mark is made on the coating and imaged simultaneously with the acquisition of fingerprint images. Such unique identification is maintained and recorded.

At block 828, the collection membrane is removed from the skin site, with DNA or RNA being acquired as described above at block 832.

Embodiments of the invention also allow for improved chain-of-custody monitoring with a variety of genetic and forensic samples. In certain jurisdictions and under certain circumstances, law-enforcement personnel may acquire both genetic and fingerprint information for comparison to existing forensic databases, as well as for the purpose of adding to such databases. In a similar way, military processing centers may acquire both genetic and fingerprint information from their own military personnel as well as from hostile forces or from suspicious parties. Other uses of genetic and fingerprint acquisition are expected to extend into a variety of civilian applications, including for use in issuing visas, for national identification, for monitoring border crossings, and the like.

Genetic-sample collection is an example of a broader class of sample collection that may be obtained in conjunction with fingerprint images according to embodiments of the invention. For example, forensic evidence such as residue on clothes or skin may be acquired for subsequent forensic analysis along with the fingerprint(s) of the person from whom the sample was taken. In this broader perspective, the acquisition of footprints mentioned above may be performed with acquisition of blood samples to be used for medical testing of various sorts, which may or may not include genetic analysis, and which may or may not include genetic fingerprinting.

There are numerous ways to acquire biological samples for genetic analysis or for other testing. In the case of DNA or RNA analysis in particular, sample methods may include blood draws, swabbing of moist tissues, skin-cell stripping or scraping, and hair-follicle collection. Generally when such samples are collected, they are placed into a container for storage and transportation prior to subsequent processing. The containers are then uniquely identified by a barcode or other type of marking.

Fingerprint acquisition is a process that has traditionally been conducted separately from the acquisition of biological or forensic samples. In processing centers such as criminal detention facilities, military processing facilities, and the like, the fingerprint acquisition has traditionally been conducted with fingerprint equipment operated by personnel using record-keeping methods that may be distinct from the equipment, personnel and record-keeping used for sample collection, with the two sets of information being combined only later. Such traditional methodologies result in correspondence error rates higher than desired, and similar correspondence errors are known to occur in other environments and with other sample types.

To reduce the possibility for mixing separately acquired fingerprint images and biological samples (including medical samples, genetic samples, forensic samples, etc.), it is desirable to have both types of information irrefutably linked together as near to the time of acquisition as possible. Embodiments of the invention accomplish this by using an imaging system that can acquire images of the biological sample container and the fingerprints simultaneously. In cases where the imaging is substantially affected by total internal reflectance, various optical coupling methods using oil and other such materials may be used to facilitate imaging of the objects. In one embodiment, the imaging system comprises a direct imaging system, which may comprise a multi-imaging system as described herein, although other embodiments may use other types of imaging systems.

Figure 9:
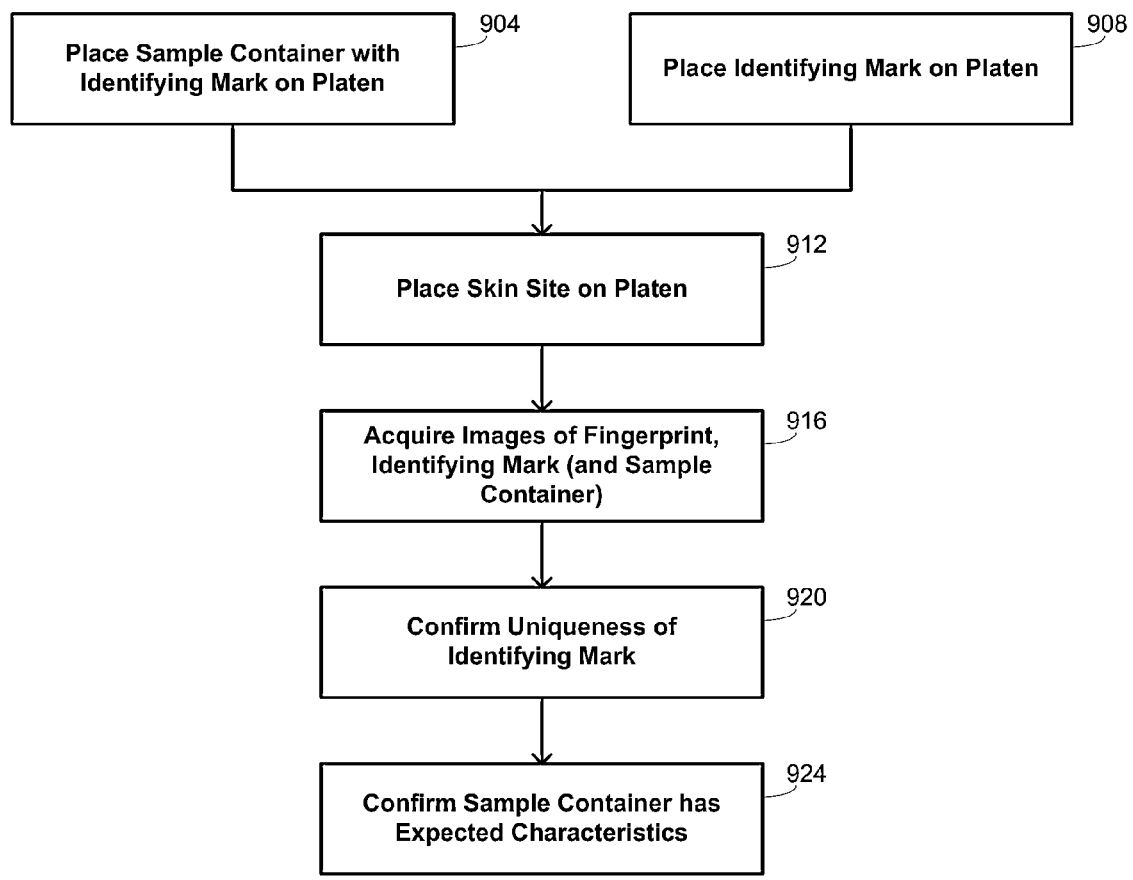
FIG. 9 is a flow diagram summarizing methods of custody-chain control according to embodiments of the invention.

Such methods of the invention are summarized with the flow diagram of FIG. 9. At block 904, a sample container that contains the sample is placed on a platen of the imaging sensor. The sample container includes an identifying mark such as a barcode or other type of mark. The sample may comprise a biological sample, a forensic sample, or some other type of sample to be associated with an individual. At block 912, a skin site of the individual is also placed on the platen, enabling acquisition of images of the fingerprint, the identifying mark, and the sample container simultaneously. In this way, subsequent retrieval and review of the fingerprint images provides a mechanism for reliably establishing correspondence with the sample at the time of fingerprint acquisition.

In some embodiments, one or more automated tests may be performed on the direct images to check for potential errors. Examples of these are provided in the drawing. For instance, at block 920, a confirmation may be made of the uniqueness of the identifying mark. That is, this check ensures that the identification mark has not previously been associated with a different fingerprint image. At block 924, checks may be performed to ensure the sample container conforms with expected characteristics. These may include, for example, that a blood vial is sufficiently full of blood, that a buccal swab container contains the swab and is properly closed, and the like.

In cases where the sample container is placed on the platen during fingerprint image acquisition, an appropriate holder or other positioning device may be designed to hold the container in a proper position and orientation. Similarly, the container may be designed for such usage with features such as a flat edge to limit rolling, a shape designed to aid proper orientation and placement on the platen, a transparent window and/or other mechanisms to facilitate automated sample checking, and other considerations of the sort.

As an alternative to placing the sample container directly on the platen during fingerprint acquisition, the identifying mark itself (or a trusted replica of such an identifying mark) may be placed on the platen. This is indicated in FIG. 9 with block 908, with the method otherwise proceeding as noted above, although the checks on the sample container at block 924 are not performed in such embodiments. These embodiments provide for trusted correspondence between the fingerprint and the identifying mark, and may be supplement with other techniques for ensuring correspondence between the sample and the identifying mark.

In certain circumstances, further linkage between samples may be effected, such as by having the individual from whom the sample was acquired sign a portion of the sample container or associated identifying mark. This signature may then be included in the combined image of the identifying mark, fingerprints, and potentially also sample container. In addition to a signature or alternatively, other identifying or relevant items may be placed on the platen for simultaneous image acquisition with the fingerprints and/or the sample. Items of interest may include an identification card such as a military identification, a driver's license, a passport, a visa, other travel documents, and others of the sort.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A method of collecting fingerprint and genetic information from an individual during a single collection session, the method comprising:
   illuminating a skin site positioned in a first position at least partially in contact with a first side of a collection membrane, the illuminating comprising passing light through a second side of the collection membrane and then through the first side of the collection membrane so as to reflect from the skin site, wherein the first and second sides face in respective opposite directions;
   obtaining an optical biometric image of the skin site by direct imaging of the skin site using the light reflected from the skin site;
   obtaining on the first side of the collection membrane, with the skin site in the first position over and at least partially in contact with the first side of the collection membrane, a cell from the skin site, wherein the collection membrane is a single-use collection membrane at least partially transparent to the light; and
   replacing the collection membrane in preparation for collecting fingerprint and genetic information from a second individual during a second collection session, wherein the collection membrane is a first collection membrane, and wherein the replacing step includes:
   removing, after the obtaining the cell from the skin site on the first side of the collection surface, the first collection membrane from an at least partially transparent platen; and
   placing, after the removing, a second collection membrane on the platen in preparation for collecting fingerprint and genetic information from the second individual during the second collection session.

2. The method recited in claim 1 wherein the collection membrane includes a chemical.

3. The method recited in claim 1 wherein the collection membrane includes an adhesive and/or an abrasive property.

4. The method recited in claim 1 further comprising applying heat and/or pressure to the skin site.

5. The method recited in claim 1 further comprising moving the skin site relative to the collection membrane.

6. The method recited in claim 1 further comprising flowing air over the skin site.

7. The method recited in claim 1 wherein illuminating the skin site comprises illuminating the skin site under a plurality of distinct optical conditions.

8. The method recited in claim 1 wherein obtaining the image of the skin site comprises generating a topographic representation of the skin site.

9. The method recited in claim 1 wherein the cell comprises a skin cell.

10. The method recited in claim 1 further comprising placing the collection membrane on the skin site.

11. The method recited in claim 10 wherein the collection membrane comprises an adhesive strip wrapped around a body part.

12. The method recited in claim 10 wherein:
the skin site comprises a portion of a hand; and
the collection membrane is comprised by a glove or finger cot.

13. The method recited in claim 10 wherein:
the collection membrane comprises a marking; and
obtaining an image of the skin site comprises obtaining an image of the marking.

14. The method recited in claim 10 wherein the collection membrane is substantially transparent to the light.

15. A method of collecting fingerprint and genetic information from an individual during a single collection session, the method comprising:
- placing a collection membrane on the skin site prior to positioning the skin site over and at least partially in contact with the collection surface wherein
- the collection membrane comprises a conformal coating having a topography that substantially matches a topography of the skin site;
- illuminating the skin site positioned in a first position at least partially in contact with a first side of the collection membrane, the illuminating comprising passing light through a second side of the collection membrane and then through the first side of the collection membrane so as to reflect from the skin site, wherein the first and second sides face in respective opposite directions; the collection surface comprising a collection membrane that permits concurrent obtaining of an optical biometric image of the skin site and retrieving of a cell of the individual
- obtaining the optical biometric image of the skin site by direct imaging of the skin site using the light reflected from the skin site, wherein the obtaining an optical biometric image of the skin site comprises obtaining an image of the conformal coating; and
- obtaining on the first side of the collection membrane, with the skin site in the first position over and at least partially in contact with the first side of the collection membrane, the cell from the skin site.

16. The method recited in claim 15 wherein the conformal coating is substantially opaque to the light.

17. A sensor comprising:
- an illumination system disposed to direct light to a skin site of an individual;
- a detection system disposed to receive light reflected from the skin site;
- a platen;
- a collection membrane that contacts the skin site and the platen during illumination of the skin site in such a way that permits, while the skin site remains positioned over and at least partially in contact with the collection membrane, both obtaining of an optical biometric image of the skin site via the collection membrane and obtaining of a cell from the individual via the collection membrane, wherein the collection membrane comprises a conformal coating having a topography that substantially matches a topography of the skin site; and
- a computational unit interfaced with the illumination system and the detection system, the computational unit having:
  - instructions to operate the illumination system to illuminate the skin site by directing the light through the platen and then through the collection membrane and to the skin site thereby causing the light to reflect from the skin site;
  - instructions to operate the detection system to generate an image of the skin site by direct imaging of the skin site using the light reflected from the skin site through the collection membrane and then through the platen, wherein the instructions to operate the detection system to generate the image of the skin site by direct imaging of the skin site using light reflected from the illuminated skin site via the collection membrane comprises instructions to operate the detection system to generate an image of the conformal coating; and
  - instructions to maintain an association between the image and the cell.

18. The sensor recited in claim 17 wherein the conformal coating is substantially opaque to the light.

19. The method recited in claim 1, further comprising before the illuminating step:
- placing the collection membrane on an at least partially transparent platen, wherein the light passes through the platen before passing through the collection membrane and then reflecting from the skin site.

20. The method recited in claim 1, wherein the skin site remains in the first position over and at least partially in contact with the first side of the collection membrane during the step of illuminating the skin site and the step of obtaining a cell on the collection membrane.

* * * * *